United States Patent
Bauer et al.

(10) Patent No.: US 11,859,059 B2
(45) Date of Patent: Jan. 2, 2024

(54) METHOD FOR THE PNEUMATIC DELIVERY OF SUPERABSORBENT PARTICLES

(71) Applicant: BASF SE, Ludwigshafen (DE)

(72) Inventors: Stephan Bauer, Ludwigshafen (DE); Katrin Baumann, Ludwigshafen (DE); Markus Toennessen, Ludwigshafen (DE); Thomas Daniel, Ludwigshafen (DE); Hanno Rüdiger Wolf, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 839 days.

(21) Appl. No.: 16/962,659

(22) PCT Filed: Jan. 28, 2019

(86) PCT No.: PCT/EP2019/051966
§ 371 (c)(1),
(2) Date: Jul. 16, 2020

(87) PCT Pub. No.: WO2019/154652
PCT Pub. Date: Aug. 15, 2019

(65) Prior Publication Data
US 2020/0347192 A1     Nov. 5, 2020

(30) Foreign Application Priority Data

Feb. 6, 2018  (EP) .................................. 18155317

(51) Int. Cl.
| | | |
|---|---|---|
| *C08J 3/12* | (2006.01) | |
| *A61L 15/60* | (2006.01) | |
| *B65G 53/10* | (2006.01) | |
| *C08L 23/08* | (2006.01) | |

(52) U.S. Cl.
CPC ............... *C08J 3/124* (2013.01); *A61L 15/60* (2013.01); *B65G 53/10* (2013.01); *C08J 2391/06* (2013.01); *C08L 23/0869* (2013.01)

(58) Field of Classification Search
CPC .......... C08J 3/12; C08J 3/124; C08J 2391/06; A61L 15/60; B65G 53/10; C08L 23/0869
USPC .......................................... 502/401
See application file for complete search history.

(56) References Cited

U.S. PATENT DOCUMENTS 5,840,321 A     11/1998 Engelhardt et al.

FOREIGN PATENT DOCUMENTS

| EP | 0755964 A2 | 1/1997 |
| WO | WO-2006/069732 A1 | 7/2006 |
| WO | WO-2008/077779 A1 | 7/2008 |

OTHER PUBLICATIONS

International Application No. PCT/EP2019/051966, International Search Report, dated Apr. 17, 2019.
Graham, et al., "Chapter 3: Commercial processes for the manufacture of superabsorbent polymers", Modern Superabsorbent Polymer Technology, ed. Buchholz et al., 1998, pp. 69-117.

*Primary Examiner* — Edward M Johnson
(74) *Attorney, Agent, or Firm* — MARSHALL, GERSTEIN & BORUN LLP (57) ABSTRACT

A method of pneumatically conveying superabsorbent particles, wherein the superabsorbent particles have been admixed with an aqueous wax dispersion prior to the pneumatic conveying, the wax has a glass transition temperature of at least 65° C. and, based on the untreated superabsorbent particles, from 0.020% to 0.20% by weight of wax has been used.

15 Claims, 3 Drawing Sheets

METHOD FOR THE PNEUMATIC DELIVERY OF SUPERABSORBENT PARTICLES

CROSS-REFERENCE TO RELATED APPLICATIONS

This is the U.S. national phase of International Application No. PCT/EP2019/051966, filed Jan. 28, 2019, which claims the benefit of European Patent Application No. 18155317.3, filed on Feb. 6, 2018.

The present invention relates to a method of pneumatically conveying superabsorbent particles, wherein the superabsorbent particles have been admixed with an aqueous wax dispersion prior to the pneumatic conveying, the wax has a glass transition temperature of at least 65° C. and, based on the untreated superabsorbent particles, from 0.020% to 0.20% by weight of wax has been used.

Superabsorbents are used to produce diapers, tampons, sanitary napkins and other hygiene articles, but also as water-retaining agents in market gardening. Superabsorbents are also referred to as water-absorbing polymers.

The production of superabsorbents is described in the monograph "Modern Superabsorbent Polymer Technology", F. L. Buchholz and A. T. Graham, Wiley-VCH, 1998, pages 71 to 103.

The coating of superabsorbents with waxes is described, for example, in EP 0 755 964 A2 and WO 2008/077779 A1.

It was an object of the present invention to provide improved superabsorbents, especially superabsorbents having improved transport properties in the case of pneumatic conveying.

The object was achieved by a method of pneumatically conveying superabsorbent particles, wherein the superabsorbent particles have been admixed with an aqueous wax dispersion prior to the pneumatic conveying, the wax has a glass transition temperature of at least 65° C. and, based on the untreated superabsorbent particles, from 0.020% to 0.20% by weight of wax has been used.

In principle, there are three distinct types of pneumatic conveying:

In dilute phase conveying, in the range of high gas velocities, the laws of the free-flowing individual particle apply as an approximation. This is the conventional type of pneumatic conveying. No product deposits whatsoever occur. There is essentially homogeneous distribution of conveyed material in the conveying conduit.

If the gas velocity falls, the conveying moves into the range of fluidized dilute phase conveying, where the conveyed material flows in the lower half of the conveying conduit in particular. In the upper half of the conveying conduit, dilute phase conveying is present.

At low gas velocities, conveying is effected exceptionally gently in the form of dense phase conveying (plug conveying, pulse conveying) with high pressure drop.

In principle, pressure conveying can work with slower conveying rates than suction conveying, since the pressure reserves are greater under elevated pressure than under reduced pressure, and since the conveying gas density which drives the product onward rises with increasing pressure.

Since conveying gas is compressible, there is not a constant pressure in the conveying conduit, but rather a higher pressure at the start than at the end. However, the gas volume also changes as a result, such that, at the start, slower gas velocities predominate at higher pressure and, at the end, higher gas velocities at lower pressure.

Excessively low conveying rates in the range of fluidized dilute phase conveying are problematic, since stable conveying is not possible in the unstable range between dense phase conveying and fluidized dilute phase conveying. Instead, the mechanical stresses which occur can lead to severe damage to the conveying system, to the extent of tearing of the conveying conduits out of the mounts.

The optimal initial gas velocity in the pneumatic conveying depends on the diameter of the conveying conduit. This dependence is best described by the Froude number:

$$Fr = \frac{v}{\sqrt{D \times g}}$$

Fr Froude number
v gas velocity
D internal diameter of the transport pipe
g acceleration due to gravity The initial gas velocity in the pneumatic conveying preferably corresponds to a Froude number of 2 to 40, most preferably of 5 to 30, most preferably of 10 to 20. The conveying material load in the pneumatic conveying is preferably from 1 to 30 kg/kg, more preferably from 5 to 25 kg/kg and most preferably from 10 to 20 kg/kg, where the conveying material load is the quotient of conveying material mass flow rate and gas mass flow rate.

The glass transition temperature of the wax is preferably at least 70° C., more preferably at least 75° C., most preferably at least 80° C.

The glass transition temperature $T_g$ is the limit to which the glass transition temperature tends as the molecular weight increases, according to G. Kanig (Kolloid-Zeitschrift & Zeitschrift für Polymere, volume 190, page 1, equation 1). $T_g$ is determined by the DSC method according to DIN ISO 11357-2:2014-07 (Differential Scanning calorimetry, 20 K/min, midpoint measurement). $T_g$ values for the homopolymers of most monomers are known and listed, for example, in Ullmann's Encyclopedia of Industrial Chemistry, VCH Weinheim, 1992, 5th ed., vol. A21, pages 169 ff.; further sources of glass transition temperatures of homopolymers are, for example, J. Brandrup, E. H. Immergut, Polymer Handbook, 15th ed., J. Wiley, New York 1996, 2nd ed., J. Wiley, New York 1975, and 3rd ed. J. Wiley, New York 1989. For the achievement of the desired glass transition temperature $T_g$ of the wax by selection of suitable types and amounts of monomers, the formula of Fox (T. G. Fox, Bull. Amer. Phys. Soc. (Ser. II) 1956, volume 1, pages 123 ff.) is helpful, according to which a good approximation of the glass transition temperature of copolymers is:

$$1/T_g = x_1/T_{g1} + x_2/T_{g2} + \ldots + x_n/T_{gn}$$

in which $x_1, x_2, \ldots x_n$ are the mass fractions of the monomers and $T_{g1}, T_{g2}, \ldots, T_{gn}$ is the glass transition temperature of the homopolymers formed in each case from one of the monomers 1, 2, ..., n in Kelvin.

The amount of wax used is preferably from 0.025% to 0.15% by weight, more preferably from 0.030% to 0.1% by weight, most preferably from 0.035% to 0.08% by weight, based in each case on the untreated superabsorbent particles.

In a preferred embodiment of the present invention, the wax is a copolymer of 70 to 95 mol % of at least one ethylenically unsaturated hydrocarbon and 5 to 30 mol % of at least one ethylenically unsaturated carboxylic acid. Very particular preference is given to ethylene-acrylic acid copolymers and ethylene-methacrylic acid copolymers.

Examples of such copolymers are Luwax® EAS 5 (BASF SE; Ludwigshafen; Germany), Nucrel® 960 (DuPont Company; Wilmington; United States of America) and Primacor® 59801 (The Dow Chemical Company; Midland; United States of America).

Preference is given to using the waxes in the form of aqueous dispersions having a solids content of preferably less than 50% by weight, more preferably less than 40% by weight and very preferably less than 30% by weight. Very preferred are wax dispersions consisting solely of water, wax and alkali metal hydroxide as dispersing aid.

Such wax dispersions are typically prepared by dispersing a wax melt in water and stabilized with suitable dispersing aids.

Examples of such wax dispersions are Poligen® WE 1, Poligen® WE 4, Poligen® CE 18 (each BASF SE; Ludwigshafen; Germany), Cohesa® 001 (Honeywell International; Morris Plains; United States of America), Michem® Emulsion 34935 (Michelman, Inc.; Cincinanati; United States of America).

In a very preferred embodiment of the present invention, aqueous wax dispersions consisting of ethylene-acrylic acid copolymer and ethylene-methacrylic acid copolymer that are subsequently stabilized solely with sodium or potassium hydroxide as dispersing aid are used.

The pH of the wax dispersion is preferably at least 7, very preferably at least 8 and most preferably at least 9.

The superabsorbent particles have a median particle size of preferably 150 to 850 µm, more preferably 200 to 600 µm and most preferably 250 to 500 µm.

In a preferred embodiment of the present invention, the superabsorbent particles have an average sphericity (AS-PHT) of preferably greater than 0.72, more preferably of greater than 0.76, most preferably of greater than 0.80.

The temperature of the superabsorbent particles during the pneumatic conveying is preferably at least 20° C., more preferably at least 30° C., most preferably at least 40° C., and preferably at least 20° C. lower, more preferably at least 25° C. lower and most preferably at least 30° C. lower than the glass transition temperature of the wax.

The present invention is based on the finding that transport properties of the superabsorbent particles can be improved by treating with an aqueous wax dispersion. Wax-coated superabsorbent particles cause a smaller pressure differential on pneumatic conveying, which increases the capacity of the conveying conduit. In order that the absorption properties of the superabsorbent particles are not adversely affected, the amount of wax must not be too high, and the wax must not form a continuous film on the particle surface. The latter is assured by a sufficiently high glass transition temperature.

The production of the superabsorbents is described in detail hereinafter:

The superabsorbents can be produced by polymerizing a monomer solution or suspension comprising
a) at least one ethylenically unsaturated monomer which bears acid groups and may have been at least partly neutralized,
b) at least one crosslinker and
c) at least one initiator,
and are typically water-insoluble.

The monomers a) are preferably water-soluble, i.e. their solubility in water at 23° C. is typically at least 1 g/100 g of water, preferably at least 5 g/100 g of water, more preferably at least 25 g/100 g of water and most preferably at least 35 g/100 g of water.

Suitable monomers a) are, for example, ethylenically unsaturated carboxylic acids, such as acrylic acid, methacrylic acid and itaconic acid. Particularly preferred monomers are acrylic acid and methacrylic acid. Very particular preference is given to acrylic acid.

The proportion of acrylic acid and/or salts thereof in the total amount of monomers a) is preferably at least 50 mol %, more preferably at least 90 mol %, most preferably at least 95 mol %.

The monomers a) typically comprise polymerization inhibitors, preferably hydroquinone monomethyl ether (MEHQ), as storage stabilizer.

The monomer solution comprises preferably up to 250 ppm by weight, preferably at most 130 ppm by weight, more preferably at most 70 ppm by weight, and preferably at least 10 ppm by weight, more preferably at least 30 ppm by weight and especially around 50 ppm by weight, of hydroquinone monomethyl ether (MEHQ), based in each case on the unneutralized monomer a). For example, the monomer solution can be prepared by using an ethylenically unsaturated monomer bearing acid groups with an appropriate content of hydroquinone monomethyl ether (MEHQ).

Suitable crosslinkers b) are compounds having at least two groups suitable for crosslinking. Such groups are, for example, ethylenically unsaturated groups which can be polymerized free-radically into the polymer chain, and functional groups which can form covalent bonds with the acid groups of the monomer a). In addition, polyvalent metal salts which can form coordinate bonds with at least two acid groups of the monomer a) are also suitable as crosslinkers b). Further suitable crosslinkers b) are the "nano-clays" described in US 2017/361305, the waterglasses described in WO 2000/31157 A1, and the aluminates described in WO 99/55767 A1.

Crosslinkers b) are preferably compounds having at least two polymerizable groups which can be polymerized free-radically into the polymer network. Suitable crosslinkers b) are, for example, ethylene glycol dimethacrylate, diethylene glycol diacrylate, polyethylene glycol diacrylate, allyl methacrylate, trimethylolpropane triacrylate, triallylamine, tetraallylammonium chloride, tetraallyloxyethane, as described in EP 0 530 438 A1, di- and triacrylates, as described in EP 0 547 847 A1, EP 0 559 476 A1, EP 0 632 068 A1, WO 93/21237 A1, WO 03/104299 A1, WO 03/104300 A1, WO 03/104301 A1 and DE 103 31 450 A1, mixed acrylates which, as well as acrylate groups, comprise further ethylenically unsaturated groups, as described in DE 103 31 456 A1 and DE 103 55 401 A1, or crosslinker mixtures, as described, for example, in DE 195 43 368 A1, DE 196 46 484 A1, WO 90/15830 A1 and WO 02/032962 A2. Preferred crosslinkers b) are pentaerythrityl triallyl ether, tetraallyloxyethane, methylenebismethacrylamide, 15-tuply ethoxylated trimethylolpropane triacrylate, polyethylene glycol diacrylate, trimethylolpropane triacrylate and triallylamine.

The amount of crosslinker b) is preferably 0.25% to 1.5% by weight, more preferably 0.3% to 1.2% by weight and most preferably 0.4% to 0.8% by weight, calculated in each case on the basis of the total amount of monomer a) used. With rising crosslinker content, centrifuge retention capacity (CRC) falls and the absorption under a pressure of 21.0 g/cm² passes through a maximum.

Initiators c) used may be all compounds which generate free radicals under the polymerization conditions, for example thermal initiators, redox initiators or photoinitiators. Suitable redox initiators are sodium peroxodisulfate/ascorbic acid, hydrogen peroxide/ascorbic acid, sodium peroxodisulfate/sodium bisulfite and hydrogen peroxide/ sodium bisulfite. Preference is given to using mixtures of thermal initiators and redox initiators, such as sodium peroxodisulfate/hydrogen peroxide/ascorbic acid. The reducing component used is preferably the disodium salt of 2-hydroxy-2-sulfonatoacetic acid or a mixture of the sodium salt of 2-hydroxy-2-sulfinatoacetic acid, the disodium salt of 2-hydroxy-2-sulfonatoacetic acid and sodium bisulfite. Such mixtures are obtainable as Brüggolite® FF6 and Brüggolite® FF7 (Brüggemann Chemicals; Heilbronn; Germany). It is alternatively possible to use pure 2-hydroxy-2-sulfonatoacetic acid or a salt thereof as reducing component, especially when ascorbic acid is also used.

It is also possible to add chelate formers and 2-hydroxycarboxylic acids to the monomer solution before or during the polymerization, as described, for example, in WO 2017/170604 A1.

Typically, an aqueous monomer solution is used. The water content of the monomer solution is preferably from 40% to 75% by weight, more preferably from 45% to 70% by weight and most preferably from 50% to 65% by weight. It is also possible to use monomer suspensions, i.e. monomer solutions with solubility-exceeding monomer a), for example sodium acrylate. As the water content rises, the energy expenditure in the subsequent drying rises and, as the water content falls, the heat of polymerization can only be removed inadequately.

The acid groups of the resulting polymer gels have typically been partly neutralized. The neutralization is conducted at the monomer stage. This is typically accomplished by mixing in the neutralizing agent as an aqueous solution or else preferably as a solid. The degree of neutralization is preferably from 25 to 85 mol %, more preferably from 30 to 80 mol % and most preferably from 40 to 75 mol %, for which the customary neutralizing agents can be used, preferably alkali metal hydroxides, alkali metal oxides, alkali metal carbonates or alkali metal hydrogencarbonates and also mixtures thereof. Instead of alkali metal salts, it is also possible to use ammonium salts. Particularly preferred alkali metals are sodium and potassium, but very particular preference is given to sodium hydroxide, sodium carbonate or sodium hydrogencarbonate and also mixtures thereof.

There follows an elucidation of solution polymerization:

Suitable reactors for solution polymerization are, for example, kneading reactors or belt reactors. In the kneader, the polymer gel formed in the polymerization of an aqueous monomer solution or suspension is comminuted continuously by, for example, contrarotatory stirrer shafts, as described in WO 2001/038402 A1. Polymerization on a belt is described, for example, in DE 38 25 366 A1 and U.S. Pat. No. 6,241,928. Polymerization in a belt reactor forms a polymer gel which has to be comminuted, for example in an extruder or kneader.

To improve the drying properties, the comminuted polymer gel obtained by means of a kneader can additionally be extruded.

The polymer gel is then typically dried with an air circulation belt drier until the residual moisture content is preferably 0.5 to 10% by weight, more preferably 1 to 6% by weight and most preferably 1.5 to 4% by weight, the residual moisture content being determined by EDANA recommended test method No. WSP 230.2-05 "Mass Loss Upon Heating". In the case of too high a residual moisture content, the dried polymer gel has too low a glass transition temperature $T_g$ and can be processed further only with difficulty. In the case of too low a residual moisture content, the dried polymer gel is too brittle and, in the subsequent comminution steps, undesirably large amounts of polymer particles with an excessively low particle size are obtained ("fines"). The solids content of the polymer gel before the drying is preferably from 25% to 90% by weight, more preferably from 35% to 70% by weight, most preferably from 40% to 60% by weight. Subsequently, the dried polymer gel is crushed and optionally coarsely comminuted.

Thereafter, the dried polymer gel is typically ground and classified, and the apparatus used for grinding may typically be single- or multistage roll mills, preferably two- or three-stage roll mills, pin mills, hammer mills or vibratory mills.

The average particle size of the polymer particles removed as the product fraction is preferably from 150 to 850 μm, more preferably from 250 to 600 μm, very particularly from 300 to 500 μm. The average particle size of the product fraction may be determined by means of EDANA recommended test method No. WSP 220.2-05 "Particle Size Distribution", where the proportions by mass of the screen fractions are plotted in cumulated form and the average particle size is determined graphically. The average particle size here is the value of the mesh size which arises for a cumulative 50% by weight.

The proportion of polymer particles having a particle size of greater than 150 μm is preferably at least 90% by weight, more preferably at least 95% by weight, most preferably at least 98% by weight.

Polymer particles with too small a particle size lower the gel bed permeability (GBP). The proportion of excessively small polymer particles ("fines") should therefore be small.

Excessively small polymer particles are therefore typically removed and recycled into the process, preferably before, during or immediately after the polymerization, i.e. prior to the drying of the polymer gel. The excessively small polymer particles can be moistened with water and/or aqueous surfactant before or during the recycling.

It is also possible to remove excessively small polymer particles in later process steps, for example after the surface postcrosslinking or another coating step. In this case, the excessively small polymer particles recycled are surface postcrosslinked or coated in another way, for example with fumed silica.

If a kneading reactor is used for polymerization, the excessively small polymer particles are preferably added during the last third of the polymerization. However, it is also possible to incorporate the excessively small polymer particles into the polymer gel in a kneader or extruder connected downstream of the polymerization reactor.

If the excessively small polymer particles are added at a very early stage, for example actually to the monomer solution, this lowers the centrifuge retention capacity (CRC) of the resulting polymer particles. However, this can be compensated, for example, by adjusting the amount of crosslinker b) used.

The proportion of polymer particles having a particle size of at most 850 μm is preferably at least 90% by weight, more preferably at least 95% by weight, most preferably at least 98% by weight.

The proportion of polymer particles having a particle size of at most 600 μm is preferably at least 90% by weight, more preferably at least 95% by weight, most preferably at least 98% by weight.

Polymer particles of excessively large particle size lower the swell rate. The proportion of excessively large polymer particles should therefore likewise be low. Excessively large polymer particles are therefore typically removed and recycled into the grinding.

There follows an elucidation of droplet polymerization:

In droplet polymerization, the monomer solution is metered into the reactor by means of at least one hole to form droplets. Droplet polymerization is described, for example, in WO 2014/079694 A1 and WO 2015/110321 A1.

The holes may, for example, be in a dropletizer plate. The number and size of the holes are selected according to the desired capacity and droplet size. The droplet diameter is typically 1.9 times the diameter of the hole. What is important here is that the liquid to be dropletized does not pass through the hole too rapidly and the pressure drop across the hole is not too great. Otherwise, the liquid is not dropletized, but rather the liquid jet is broken up (sprayed) owing to the high kinetic energy. The Reynolds number based on the throughput per hole and the hole diameter is preferably less than 2000, more preferably less than 1600, especially preferably less than 1400 and most preferably less than 1200.

The dropletizer plate has preferably at least 5, more preferably at least 25 and most preferably at least 50 holes, and preferably up to 750, more preferably up to 500 and most preferably up to 250 holes. The diameter of the holes is selected according to the desired droplet size.

The diameter of the holes is preferably from 50 to 500 µm, more preferably from 100 to 300 µm and most preferably from 150 to 250 µm. The distance between the holes is preferably 10 to 50 mm, more preferably 12 to 40 mm and most preferably 15 to 30 mm. Excessively small distances lead to formation of agglomerates.

The temperature of the monomer solution on passage through the holes is preferably from 5 to 80° C., more preferably from 10 to 70° C. and most preferably from 30 to 60° C.

A carrier gas flows through the reactor. This carrier gas can be conducted through the reactor in cocurrent or in countercurrent to the free-falling droplets of the monomer solution, preferably in cocurrent, i.e. from the bottom upward. After one pass, the carrier gas is preferably recycled at least partly into the reactor as cycle gas, preferably to an extent of at least 50% and more preferably to an extent of at least 75%. Typically, a portion of the carrier gas is discharged after each pass, preferably up to 10%, more preferably up to 3% and most preferably up to 1%.

The oxygen content of the carrier gas is preferably from 0.5 to 15% by volume, more preferably from 1 to 10% by volume and most preferably from 2 to 7% by volume.

As well as oxygen, the carrier gas preferably comprises nitrogen. The nitrogen content of the carrier gas is preferably at least 80% by volume, more preferably at least 90% by volume and most preferably at least 95% by volume. It is also possible to use gas mixtures. The carrier gas may also be laden with steam and/or acrylic acid vapors.

The gas velocity is preferably set such that the flow in the reactor is directed, for example no convection currents opposed to the general flow direction are present, and is typically 0.1 to 2.5 m/s, preferably 0.3 to 1.5 m/s, more preferably from 0.5 to 1.2 m/s, especially preferably 0.6 to 1.0 m/s and most preferably 0.7 to 0.9 m/s.

The carrier gas flowing through the reactor is appropriately preheated to the reaction temperature upstream of the reactor.

Advantageously, the gas inlet temperature is regulated such that the gas outlet temperature, i.e. the temperature with which the carrier gas leaves the reactor, is typically from 90 to 150° C., preferably from 100 to 140° C., more preferably from 105 to 135° C., especially preferably from 110 to 130° C. and most preferably from 115 to 125° C.

The reaction can be performed under elevated pressure or under reduced pressure; a reduced pressure of down to 100 mbar relative to ambient pressure is preferred.

The reaction offgas, i.e. the gas leaving the reactor, can, for example, be cooled in a heat exchanger. This condenses water and unconverted monomer a). Thereafter, the reaction offgas can at least partly be reheated and recycled into the reactor as cycle gas. A portion of the reaction offgas can be discharged and replaced by fresh carrier gas, in which case water and unconverted monomers a) present in the reaction offgas can be removed and recycled.

Particular preference is given to an integrated heating system, which means that some of the waste heat in the cooling of the offgas is used to heat the cycle gas.

The reactors may be trace-heated. The trace heating is adjusted such that the wall temperature is at least 5° C. above the internal reactor temperature, and condensation at the reactor walls is reliably prevented.

There follows a description of inverse suspension polymerization:

Inverse suspension polymerization involves suspending the monomer solution in a hydrophobic solvent during the polymerization. Inverse suspension polymerization is described, for example, in WO 2008/068208 A1 and WO 2015/062883 A2.

Usable hydrophobic solvents are all the solvents known to the person skilled in the art for use in suspension polymerization. Preference is given to using aliphatic hydrocarbons, such as n-hexane, n-heptane, n-octane, n-nonane, n-decane, cyclohexane or mixtures thereof. Hydrophobic solvents have a solubility in water at 23° C. of less than 5 g/100 g, preferably less than 1 g/100 g, more preferably less than 0.5 g/100 g.

The hydrophobic solvent boils within the range from preferably 50 to 150° C., more preferably 60 to 120° C., most preferably 70 to 90° C.

The ratio between hydrophobic solvent and monomer solution is 0.5 to 3, preferably 0.7 to 2.5 and very preferably from 0.8 to 2.2.

The mean diameter of the monomer solution droplets in the suspension, if no agglomeration is conducted, is preferably at least 100 µm, more preferably from 100 to 1000 µm, more preferably from 150 to 850 µm, most preferably from 300 to 600 µm, the droplet diameter being determinable by light scattering and signifying the volume-average mean diameter.

The diameter of the monomer solution droplets can be adjusted via the stirrer energy introduced and through suitable dispersing aids.

For dispersion of the aqueous monomer solution in the hydrophobic solvent or for dispersion of the resultant superabsorbent particles, preference is given to adding dispersing aids. These dispersing aids may be anionic, cationic, nonionic or amphoteric surfactants, or natural, semisynthetic or synthetic polymers.

Anionic surfactants are, for example, sodium polyoxyethylene dodecyl ether sulfate and sodium dodecyl ether sulfate. A cationic surfactant is, for example, trimethylstearylammonium chloride. An amphoteric surfactant is, for example, carboxymethyldimethylcetylammonium. Nonionic surfactants are, for example, sucrose fatty acid esters, such as sucrose monostearate and sucrose dilaurate, sorbitan esters such as sorbitan monostearate, polyoxyalkylene compounds based on sorbitan esters, such as polyoxyethylene-sorbitan monostearate.

The dispersing aid is typically dissolved or dispersed in the hydrophobic solvent. The dispersing aid is used in amounts between 0.01% and 10% by weight, preferably between 0.2% and 5% by weight and more preferably between 0.5% and 2% by weight, based on the monomer solution. The diameter of the monomer solution droplets can be adjusted via the type and amount of dispersing aid.

Advantageously, several stirred reactors are connected in series for the polymerization. Through postreaction in further stirred reactors, the monomer conversion can be increased and backmixing can be reduced. In this context, it is additionally advantageous when the first stirred reactor is not too large. With increasing size of the stirred reactor, there is inevitably broadening of the size distribution of the dispersed monomer solution droplets. A relatively small first reactor therefore enables the production of superabsorbent particles with a particularly narrow particle size distribution.

The reaction is preferably conducted under reduced pressure, for example at a pressure of 800 mbar. The pressure can be used to set the boiling point of the reaction mixture to the desired reaction temperature.

If the polymerization is conducted under adequate reflux, the inertization can be dispensed with. In this case, the dissolved oxygen is removed from the polymerization reactor together with the evaporating solvent.

The superabsorbent particles may be azeotropically dewatered in the polymer dispersion and separated from the polymer dispersion, and the separated superabsorbent particles may be dried to remove the adhering residual hydrophobic solvent.

There follows a description of surface postcrosslinking:

To further improve the properties, the polymer particles can be thermally surface postcrosslinked. Suitable surface postcrosslinkers are compounds which comprise groups which can form covalent bonds with at least two carboxylate groups of the polymer particles. Suitable compounds are, for example, polyfunctional amines, polyfunctional amido amines, polyfunctional epoxides, as described in EP 0 083 022 A2, EP 0 543 303 A1 and EP 0 937 736 A2, di- or polyfunctional alcohols, as described in DE 33 14 019 A1, DE 35 23 617 A1 and EP 0 450 922 A2, β-hydroxyalkylamides, as described in DE 102 04 938 A1 and U.S. Pat. No. 6,239,230, or oxazolines, as described in EP 0 999 238 A2.

Additionally described as suitable surface postcrosslinkers are cyclic carbonates in DE 40 20 780 C1, 2-oxazolidinone and derivatives thereof, such as 2-hydroxyethyl-2-oxazolidinone, in DE 198 07 502 A1, bis- and poly-2-oxazolidinones in DE 198 07 992 C1, 2-oxotetrahydro-1,3-oxazine and derivatives thereof in DE 198 54 573 A1, N-acyl-2-oxazolidinones in DE 198 54 574 A1, cyclic ureas in DE 102 04 937 A1, bicyclic amido acetals in DE 103 34 584 A1, oxetanes and cyclic ureas in EP 1 199 327 A2, oxetanes in EP 2 204 388 A1, and morpholine-2,3-dione and derivatives thereof in WO 03/031482 A1.

Preferred surface postcrosslinkers are ethylene carbonate, ethylene glycol diglycidyl ether, reaction products of polyamides with epichlorohydrin and mixtures of propylene glycol and butane-1,4-diol.

Very particularly preferred surface postcrosslinkers are 2-hydroxyethyl-2-oxazolidinone, 2-oxazolidinone and propane-1,3-diol.

In addition, it is also possible to use surface postcrosslinkers which comprise additional polymerizable ethylenically unsaturated groups, as described in DE 37 13 601 A1.

The amount of surface postcrosslinker is preferably 0.001% to 3% by weight, more preferably 0.02% to 1% by weight and most preferably 0.05% to 0.2% by weight, based in each case on the polymer particles.

The surface postcrosslinking is typically performed in such a way that a solution of the surface postcrosslinker is sprayed onto the dried polymer particles. After the spray application, the polymer particles coated with surface postcrosslinker are surface postcrosslinked and dried, and the surface postcrosslinking reaction can take place both before and during the drying.

The spray application of a solution of the surface postcrosslinker is preferably performed in mixers with moving mixing tools, such as screw mixers, disk mixers and paddle mixers. Particular preference is given to horizontal mixers such as paddle mixers, very particular preference to vertical mixers. The distinction between horizontal mixers and vertical mixers is made by the position of the mixing shaft, i.e. horizontal mixers have a horizontally mounted mixing shaft and vertical mixers have a vertically mounted mixing shaft. Suitable mixers are, for example, horizontal Pflugschar® plowshare mixers (Gebr. Lödige Maschinenbau GmbH; Paderborn; Germany), Vrieco-Nauta continuous mixers (Hosokawa Micron BV; Doetinchem; the Netherlands), Processall Mixmill mixers (Processall Incorporated; Cincinnati; USA) and Schugi Flexomix® (Hosokawa Micron BV; Doetinchem; the Netherlands). However, it is also possible to spray on the surface postcrosslinker solution in a fluidized bed.

The surface postcrosslinkers are typically used in the form of an aqueous solution. The penetration depth of the surface postcrosslinker into the polymer particles can be adjusted via the content of nonaqueous solvent and total amount of solvent.

When exclusively water is used as the solvent, a surfactant is advantageously added. This improves the wetting characteristics and reduces the tendency to form lumps. However, preference is given to using solvent mixtures, for example isopropanol/water, propane-1,3-diol/water, propylene glycol/water, 2-methylpropane-1,3-diol/water, ethylene glycol/water, diethylene glycol/water, triethylene glycol/water, tetraethylene glycol/water, or polyethylene glycol/water, where the mass mixing ratio is preferably from 20:80 to 40:60.

The surface postcrosslinking is preferably performed in contact dryers, more preferably paddle dryers, most preferably disk dryers. Suitable dryers are, for example, Hosokawa Bepex® Horizontal Paddle Dryer (Hosokawa Micron GmbH; Leingarten; Germany), Hosokawa Bepex® Disk Dryer (Hosokawa Micron GmbH; Leingarten; Germany), Holo-Flite® dryers (Metso Minerals Industries Inc.; Danville; USA) and Nara Paddle Dryer (NARA Machinery Europe; Frechen; Germany). Moreover, fluidized bed dryers may also be used.

The surface postcrosslinking can be effected in the mixer itself, by heating the jacket or blowing in warm air. Equally suitable is a downstream dryer, for example a tray dryer, a rotary tube oven or a heatable screw. It is particularly advantageous to effect mixing and thermal surface postcrosslinking in a fluidized bed dryer.

Preferred reaction temperatures are in the range of 100 to 250° C., preferably 120 to 220° C., more preferably 130 to 210° C., most preferably 150 to 200° C. The preferred dwell time at this temperature is preferably at least 10 minutes, more preferably at least 20 minutes, most preferably at least 30 minutes, and typically at most 60 minutes.

In a preferred embodiment of the present invention, the polymer particles are cooled after the surface postcrosslinking. The cooling is preferably performed in contact coolers, more preferably paddle coolers and most preferably disk coolers. Suitable coolers are, for example, Hosokawa Bepex® Horizontal Paddle Cooler (Hosokawa Micron GmbH; Leingarten; Germany), Hosokawa Bepex® Disk Cooler (Hosokawa Micron GmbH; Leingarten; Germany), Holo-Flite® coolers (Metso Minerals Industries Inc.; Danville; USA) and Nara Paddle Cooler (NARA Machinery Europe; Frechen; Germany). Moreover, fluidized bed coolers may also be used.

In the cooler, the polymer particles are cooled to preferably 40 to 90° C., more preferably 45 to 80° C., most preferably 50 to 70° C.

To further improve the properties, the polymer particles can be coated or remoisturized.

The remoisturizing is preferably performed at 40 to 120° C., more preferably at 50 to 110° C., most preferably at 60 to 100° C. At excessively low temperatures the polymer particles tend to form lumps, and at higher temperatures water already evaporates to a noticeable degree. The amount of water used for remoisturizing is preferably from 1% to 15% by weight, more preferably from 2% to 10% by weight and most preferably from 3% to 8% by weight. The remoisturizing increases the mechanical stability of the polymer particles and reduces their tendency to static charging.

Suitable coatings for improving the swell rate and the gel bed permeability (GBP) are, for example, inorganic inert substances, such as water-insoluble metal salts, organic polymers, cationic polymers and di- or polyvalent metal cations. Suitable coatings for dust binding are, for example, polyols. Suitable coatings for counteracting the undesired caking tendency of the polymer particles are, for example, fumed silica, such as Aerosil® 200, and surfactants, such as Span® 20. Suitable coatings for dust binding, for reducing the tendency to caking and for increasing the mechanical stability are polymer dispersions as described in EP 0 703 265 B1, and waxes as described in U.S. Pat. No. 5,840,321.

Methods:

The standard test methods described hereinafter and designated "WSP" are described in: "Standard Test Methods for the Nonwovens Industry", 2005 edition, published jointly by the Worldwide Strategic Partners EDANA (Avenue Eugene Plasky, 157, 1030 Brussels, Belgium, www.edana.org) and INDA (1100 Crescent Green, Suite 115, Cary, North Carolina 27518, USA, www.inda.org). This publication is obtainable both from EDANA and from INDA.

The measurements should, unless stated otherwise, be conducted at an ambient temperature of 23±2° C. and a relative air humidity of 50±10%. The superabsorbent particles are mixed thoroughly before the measurement.

Residual Monomers

The residual monomer content is determined by EDANA recommended test method No. WSP 210.2 (05) "Residual Monomers".

Moisture Content

Moisture content is determined by EDANA recommended test method No. WSP 230.2 (05) "Mass Loss Upon Heating".

Centrifuge Retention Capacity

Centrifuge retention capacity (CRC) is determined by EDANA recommended test method No. WSP 241.2 (05) "Fluid Retention Capacity in Saline, After Centrifugation".

Absorption Under a Pressure of 21.0 g/Cm² (Absorption Under Load)

Absorption under a pressure of 21.0 g/cm² (AUL) is determined by EDANA recommended test method No. WSP 242.2 (05) "Absorption Under Pressure, Gravimetric Determination".

Absorption Under a Pressure of 49.2 g/Cm² (Absorption Under High Load)

Absorption under a pressure of 49.2 g/cm² (AUHL) is determined analogously to EDANA recommended test method No. WSP 242.2 (05) "Absorption Under Pressure, Gravimetric Determination", except that a pressure of 49.2 g/cm² (0.7 psi) is established rather than a pressure of 21.0 g/cm² (0.3 psi).

Extractables

The content of extractables of the water-absorbing polymer particles is determined by EDANA recommended test method No. WSP 270.2 (05) "Extractable".

Bulk Density

Bulk density (ASG) is determined by EDANA recommended test method No. WSP 260.2 (05) "Density, Gravimetric Determination".

Saline Flow Conductivity

The saline flow conductivity (SFC) of a swollen gel layer under a pressure of 0.3 psi (2070 Pa) is, as described in EP 0 640 330 A1, determined as the gel layer permeability of a swollen gel layer of water-absorbing polymer particles, the apparatus described on page 19 and in FIG. 8 in the cited patent application having been modified such that the glass frit (40) is no longer used, and the plunger (39) consists of the same polymer material as the cylinder (37) and now comprises 21 bores of equal size distributed homogeneously over the entire contact area. The procedure and evaluation of the measurement remain unchanged from EP 0 640 330 A1. The flow is detected automatically.

Saline flow conductivity (SFC) is calculated as follows:

$$\text{SFC}[\text{cm}^3\text{s/g}] = (Fg(t=0) \times L_0)/(d \times A \times WP)$$

where $Fg(t=0)$ is the flow of NaCl solution in g/s, which is obtained using linear regression analysis of the $Fg(t)$ data of the flow determinations by extrapolation to $t=0$, $L_0$ is the thickness of the gel layer in cm, d is the density of the NaCl solution in g/cm³, A is the area of the gel layer in cm², and WP is the hydrostatic pressure over the gel layer in dyn/cm².

Vortex Test 50.0 ml±1.0 ml of a 0.9% by weight aqueous sodium chloride solution are introduced into a 100 ml beaker which comprises a magnetic stirrer bar of size 30 mm×6 mm. A magnetic stirrer is used to stir the sodium chloride solution at 600 rpm. Then 2000 g±0.010 g of water-absorbing polymer particles is added as rapidly as possible, and the time taken for the stirrer vortex to disappear as a result of the absorption of the sodium chloride solution by the water-absorbing polymer particles is measured. When measuring this time, the entire contents of the beaker may still be rotating as a homogeneous gel mass, but the surface of the gelated sodium chloride solution must no longer exhibit any individual turbulences. The time taken is reported as the vortex.

Average Sphericity (ASPHT)

Average sphericity (ASPHT) is determined with the PartAn® 3001 L particle analyzer (Microtrac Europe GmbH; Germany).

The sample to be analyzed is introduced into a funnel. The computer-controlled measurement system starts the metering device and ensures a continuous, concentration-regulated particle flow. The particles fall individually through the measurement shaft and generate high-contrast shadow images between light source and high-resolution camera. The light source is actuated by the camera and, because of very short exposure times, produces faultless image information for the multiple evaluation of each individual particle in real time.

In a 3D process, each particle is analyzed repeatedly and the process thus gives the absolute results for length, width, thickness, area and circumference. The number of pixels covered by the particle is used to calculate the size and shape.

Average Particle Size

Average particle size is determined by means of EDANA recommended test method No. WSP 220.2 (05) "Particle Size Distribution", by plotting the proportions by mass of the screen fractions in cumulated form and determining the average particle size from the graph. The average particle size here is the value of the mesh size which arises for a cumulative 50% by weight.

Dust Measurement

Figure 1:
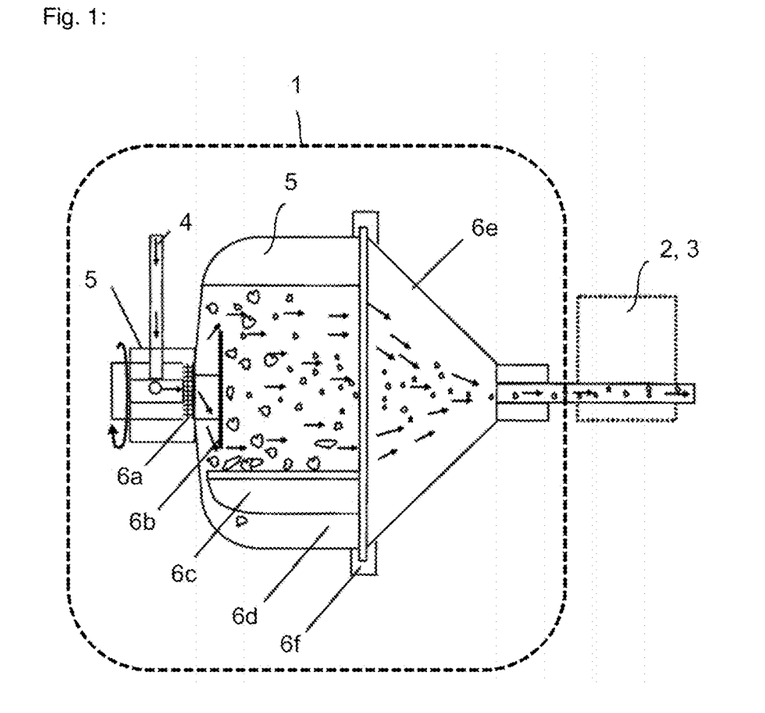

Dust measurement is conducted with a dustmeter (Heubach GmbH, Langelsheim, Germany). FIG. 1 shows the schematic setup of the dustmeter (1) in combination with a Welas® 2070 aerosol sensor with optical fiber (2) and a Promo® 3000 H scattered light aerosol spectrometer system (3) (Pelas GmbH, Karlsruhe, Germany). The supply of dry air (<10% relative humidity) as transport gas is adjusted to 0.1 mbar and a flow rate of 1.00 m³ (STP)/h via the control valve (4) and introduced into the dustmeter via the air suction stub (5). For the measurement, 25±1 g of superabsorbent was introduced into a modified vessel (6). The vessel (6) consists of a drum (6a) having a length of 60 mm and a diameter of 140 mm, a guard screen (6b), a baffle plate (6c), 3 lifting flights in a length of 60 mm and a height of 22 mm (6d), a lid (6e) and a clamp device (6f). The speed of the vessel (6) during the measurement was 45 rpm.

The number of dust particles was counted with the aid of the Promo® 3000 H scattered light aerosol spectrometer system over a period of 10 min and normalized to 1 g of superabsorbent per minute. The dust particles were classified into 3 classes:

Class a) <1 μm
Class b) 1-10 μm
Class c) >10 μm

EXAMPLES

Example 1

A superabsorbent was produced analogously to example 1 of WO 2016/134905 A1. The monomer solution used additionally comprised 1.07% by weight of the disodium salt of 1-hydroxyethylidene-1,1-diphosphonic acid.

The gas inlet temperature of reaction zone (5) was 167° C., the gas outlet temperature of reaction zone (5) was 107° C., the gas inlet temperature of the internal fluidized bed (27) was 100° C., the product temperature in the internal fluidized bed (27) was 78° C., the gas outlet temperature of the condensation column (12) was 57° C., and the gas outlet temperature of the gas drying unit (37) was 47° C.

The superabsorbent produced (base polymer) had a bulk density (ASG) of 0.73 g/ml, a centrifuge retention capacity (CRC) of 49.4 g/g, an absorption under a pressure of 21.0 g/cm² (AUL) of 10.5 g/g, a residual monomer content of 5200 ppm, an extractables content of 4.5% by weight and a moisture content of 8.0% by weight.

The superabsorbent had the following particle size distribution:

| | |
|---|---|
| >1000 μm | 0.3% by weight |
| 850-1000 μm | 1.1% by weight |
| 600-850 μm | 3.7% by weight |
| 500-600 μm | 9.9% by weight |
| 400-500 μm | 32.8% by weight |
| 300-400 μm | 40.4% by weight |
| 250-300 μm | 6.4% by weight |
| 200-250 μm | 4.1% by weight |
| 106-200 μm | 1.2% by weight |
| <106 μm | 0.1% by weight |

The superabsorbent had a median particle size (d50) of 377 μm and an average sphericity (ASPHT) of 0.81.

The base polymer was subsequently surface postcrosslinked analogously to examples 11 to 15 of WO 2015/110321 A1. 2.0% by weight of ethylene carbonate, 5.0% by weight of water and 0.3% by weight of aluminum sulfate were used, based in each case on the base polymer. The product temperature was 160° C. and the height of the weir was 75%.

In the cooler, after the surface postcrosslinking, first 2.35% by weight of a 0.2% by weight aqueous solution of sorbitan monolaurate and then 2.35% by weight of a dilute aqueous polymer dispersion of Poligen® CE 18 (BASF SE; Ludwigshafen; Germany) were added. Poligen® CE 18 is a 21% by weight aqueous wax dispersion of an ethylene-acrylic acid copolymer composed of 20% by weight of acrylic acid and 80% by weight of ethylene, stabilized with potassium hydroxide. The wax has a glass transition temperature of 80° C. The dilute aqueous polymer dispersion was calculated such that 500 ppm of wax was added in solid form, based on the superabsorbent particle on the polymer.

The temperature of the superabsorbent particles at the time of addition was 75° C.

The surface postcrosslinked superabsorbent produced had a bulk density (ASG) of 0.794 g/ml, a centrifuge retention capacity (CRC) of 40.1 g/g, an absorption under a pressure of 21.0 g/cm² (AUL) of 32.9 g/g, an absorption under a pressure of 49.2 g/cm² (AUHL) of 23.3 g/g, a saline flow conductivity (SFC) of $5\times10^{-7}$ cm³s/g, a vortex of 68 s, a moisture content of 3.2% by weight, a residual monomer content of 399 ppm and an extractables content of 3.2% by weight.

The surface postcrosslinked superabsorbent had the following particle size distribution:

| | |
|---|---|
| >850 μm | 0.0% by weight |
| 710-850 μm | 0.4% by weight |
| 600-710 μm | 2.2% by weight |
| 500-600 μm | 9.0% by weight |
| 400-500 μm | 36.4% by weight |
| 300-400 μm | 39.2% by weight |
| 250-300 μm | 7.0% by weight |
| 200-250 μm | 4.0% by weight |
| 150-200 μm | 1.5% by weight |
| <150 μm | 0.2% by weight |

The superabsorbent had a median particle size (d50) of 379 μm and an average sphericity (ASPHT) of 0.80.

Subsequently, the superabsorbent particles were pneumatically conveyed.

The conveying conduit used was a smooth pipeline of aluminum having a length of 164 m and an internal diameter of 100 mm. The conveying conduit consisted of two horizontal and two vertical sections, with the sections connected by bends. The total vertical height gain was 13 m. The conveying conduit had an internal bypass of the Intraflow type (Zeppelin Systems GmbH; Friedrichshafen; Germany). The product was conveyed into the conveying conduit by means of a CFH250 star feeder (Zeppelin Systems GmbH; Friedrichshafen; Germany).

The conveying output was 7.5 t/h of superabsorbent particles, the speed of the star feeder was 13.5 rpm, the conveying air rate was 560 m³ (STP)/h, and the gas velocity was 11 m/s at the start of the conveying conduit and 11.1 m/s at the end of the conveying conduit. The pressure in the conveying conduit was from +660 to 0 mbar, based on the ambient pressure. During the stable conveying, the pressure fluctuations were ±50 mbar and the average pressure in the conveying was 560 mbar. The conveying material load was 11 kg/kg, and the Froude number at the start of the conveying was 11.

After the conveying, the superabsorbent had a centrifuge retention capacity (CRC) of 39.5 g/g, an absorption under a pressure of 21.0 g/cm² (AUL) of 31.1 g/g, an absorption under a pressure of 49.2 g/cm² (AUHL) of 23.1 g/g, a saline flow conductivity (SFC) of $4 \times 10^{-7}$ cm³s/g.

Figure 2:
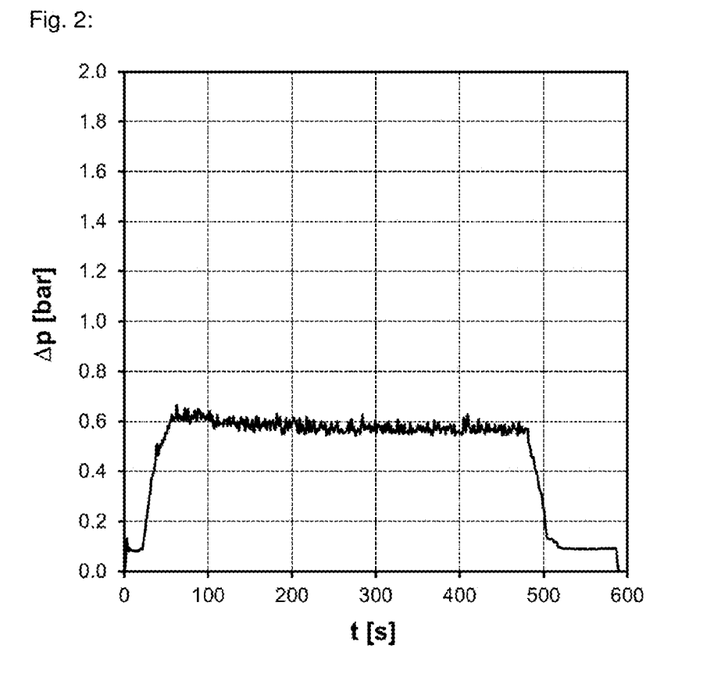

The starting pressure in the conveying conduit as a function of time is shown in FIG. 2.

The number of dust particles of example 1 before and after the pneumatic conveying is collated in table 1.

Example 2 (Comparative Example)

The procedure was as in example 1. The amount of Poligen® CE 18 added was lowered to 125 ppm, based on the superabsorbent particles.

The surface postcrosslinked superabsorbent produced had a bulk density (ASG) of 0.761 g/ml, a centrifuge retention capacity (CRC) of 39.3 g/g, an absorption under a pressure of 21.0 g/cm² (AUL) of 32.7 g/g, an absorption under a pressure of 49.2 g/cm² (AUHL) of 23.1 g/g, a saline flow conductivity (SFC) of $5 \times 10^{-7}$ cm³s/g, a vortex of 65 s, a moisture content of 3.1% by weight, a residual monomer content of 428 ppm and an extractables content of 3.0% by weight.

The surface postcrosslinked superabsorbent had the following particle size distribution:

| | |
|---|---|
| >850 µm | 0.0% by weight |
| 710-850 µm | 0.4% by weight |
| 600-710 µm | 2.9% by weight |
| 500-600 µm | 8.6% by weight |
| 400-500 µm | 36.4% by weight |
| 300-400 µm | 39.5% by weight |
| 250-300 µm | 6.8% by weight |
| 200-250 µm | 3.8% by weight |
| 150-200 µm | 1.1% by weight |
| <150 µm | 0.3% by weight |

The superabsorbent had a median particle size (d50) of 380 µm and an average sphericity (ASPHT) of 0.80.

The conveying output was 7.6 t/h of superabsorbent particles, the speed of the star feeder was 13.5 rpm, the conveying air rate was 560 m³ (STP)/h, and the gas velocity was now 7.7 m/s at the start of the conveying conduit and 16.4 m/s at the end of the conveying conduit. The pressure in the conveying conduit was from +1600 to 0 mbar, based on the ambient pressure. The conveying material load was 12 kg/kg, and the Froude number at the start of the conveying was 7.7.

Uniform operation of the pneumatic conveying with a conveying air rate of 560 m³ (STP)/h was not possible. During the unstable conveying, the pressure fluctuations were ±450 mbar and the average pressure in the conveying was 1120 mbar.

After the conveying, the superabsorbent had a centrifuge retention capacity (CRC) of 39.3 g/g, an absorption under a pressure of 21.0 g/cm² (AUL) of 30.7 g/g, an absorption under a pressure of 49.2 g/cm² (AUHL) of 21.6 g/g, a saline flow conductivity (SFC) of $3 \times 10^{-7}$ cm³s/g.

Figure 3:
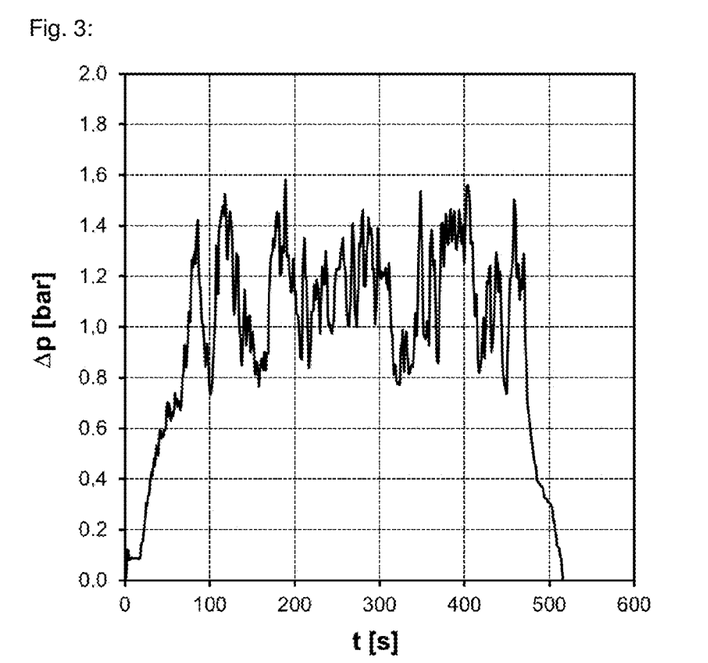

The starting pressure in the conveying conduit as a function of time is shown in FIG. 3.

The number of dust particles of example 2 before and after the pneumatic conveying is collated in table 1.

Example 3 (Comparative Example)

The procedure was as in example 1. No Poligen® CE 18 was added.

The surface postcrosslinked superabsorbent produced had a bulk density (ASG) of 0.78 g/ml, a centrifuge retention capacity (CRC) of 39.6 g/g, an absorption under a pressure of 21.0 g/cm² (AUL) of 33.2 g/g, an absorption under a pressure of 49.2 g/cm² (AUHL) of 24.8 g/g, a saline flow conductivity (SFC) of $5 \times 10^{-7}$ cm³s/g, a vortex of 66 s, a moisture content of 3.5% by weight, a residual monomer content of 386 ppm and an extractables content of 3.0% by weight.

The surface postcrosslinked superabsorbent had the following particle size distribution:

| | |
|---|---|
| >850 µm | 0.0% by weight |
| 710-850 µm | 0.4% by weight |
| 600-710 µm | 2.3% by weight |
| 500-600 µm | 10.0% by weight |
| 400-500 µm | 36.3% by weight |
| 300-400 µm | 39.4% by weight |
| 250-300 µm | 6.0% by weight |
| 200-250 µm | 4.1% by weight |
| 150-200 µm | 1.3% by weight |
| <150 µm | 0.2% by weight |

The superabsorbent had a median particle size (d50) of 383 µm and an average sphericity (ASPHT) of 0.79.

The conveying output was 7.2 t/h of superabsorbent particles, the speed of the star feeder was 13.5 rpm, the conveying air rate was 560 m³ (STP)/h, and the gas velocity was now 7.5 m/s at the start of the conveying conduit and 16.4 m/s at the end of the conveying conduit. The pressure in the conveying conduit was from 2400 to 0 mbar, based on the ambient pressure. During the conveying, the pressure fluctuations were ±1000 mbar. The conveying material load was 11.3 kg/kg, and the Froude number at the start of the conveying was 7.5. The pressure peaks during the conveying were clearly audible in the form of loud banging in the conduit.

Uniform operation of the pneumatic conveying with a conveying air rate of 560 m³ (STP)/h was not possible. During the very unstable conveying, the pressure fluctuations were ±900 mbar and the average pressure in the conveying was 1160 mbar.

After the conveying, the superabsorbent had a centrifuge retention capacity (CRC) of 38.6 g/g, an absorption under a pressure of 21.0 g/cm² (AUL) of 32.0 g/g, an absorption under a pressure of 49.2 g/cm² (AUHL) of 20.6 g/g, a saline flow conductivity (SFC) of $2 \times 10^{-7}$ cm³s/g.

Figure 4:
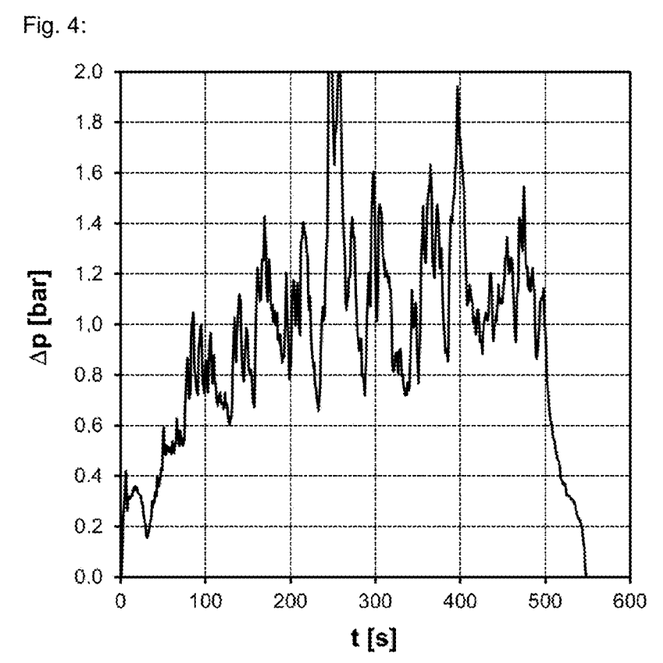

The starting pressure in the conveying conduit as a function of time is shown in FIG. 4.

The number of dust particles of example 3 before and after the pneumatic conveying is collated in table 1.

Example 4

The base polymer from example 1 was subsequently surface postcrosslinked analogously to examples 11 to 15 of WO 2015/110321 A1. 2.0% by weight of ethylene carbonate, 5.0% by weight of water and 0.05% by weight of aluminum sulfate were used, based in each case on the base polymer. The product temperature was 159° C. and the height of the weir was 75%.

In the cooler, after the surface postcrosslinking, first 4.35% by weight of a 0.23% by weight aqueous solution of aluminum lactate and then 1.66% by weight of a dilute aqueous polymer dispersion of Poligen® CE 18 (BASF SE; Ludwigshafen; Germany) and sorbitan monolaurate were added. The dilute aqueous polymer dispersion was calculated such that 500 ppm of wax in solid form and 25 ppm of sorbitan monolaurate were added, based on the superabsorbent particles.

The surface postcrosslinked superabsorbent produced had a bulk density (ASG) of 0.75 g/ml, a centrifuge retention capacity (CRC) of 38.1 g/g, an absorption under a pressure of 21.0 g/cm$^2$ (AUL) of 34.4 g/g, an absorption under a pressure of 49.2 g/cm$^2$ (AUHL) of 25.9 g/g, a saline flow conductivity (SFC) of 5×10$^{-7}$ cm$^3$s/g, a vortex of 69 s, a moisture content of 4.5% by weight, a residual monomer content of 263 ppm and an extractables content of 2.6% by weight.

The surface postcrosslinked superabsorbent had the following particle size distribution:

| | |
|---|---|
| >850 μm | 0.0% by weight |
| 710-850 μm | 0.1% by weight |
| 600-710 μm | 2.5% by weight |
| 500-600 μm | 12.5% by weight |
| 400-500 μm | 38.2% by weight |
| 300-400 μm | 37.4% by weight |
| 250-300 μm | 5.0% by weight |
| 200-250 μm | 3.0% by weight |
| 150-200 μm | 0.6% by weight |
| <150 μm | 0.2% by weight |

The superabsorbent had a median particle size (d50) of 396 μm and an average sphericity (ASPHT) of 0.80.

The superabsorbent particles thus obtained were pneumatically conveyed under different conditions (examples 4a to 4d).

Example 4 a

The conveying output in the first conveying operation was 7.2 t/h of superabsorbent particles, the speed of the star feeder was 13.5 rpm, the conveying air rate was 550 m$^3$ (STP)/h, and the gas velocity was now 10.7 m/s at the start of the conveying conduit and 17.3 m/s at the end of the conveying conduit. The pressure in the conveying conduit was from 740 to 0 mbar, based on the ambient pressure. The conveying material load was 10.9 kg/kg, and the Froude number at the start of the conveying was 11. During the stable conveying, the pressure fluctuations were ±50 mbar and the average pressure in the conveying was 580 mbar.

After the conveying, the superabsorbent had a centrifuge retention capacity (CRC) of 38.7 g/g, an absorption under a pressure of 21.0 g/cm$^2$ (AUL) of 34.2 g/g, an absorption under a pressure of 49.2 g/cm$^2$ (AUHL) of 26.2 g/g, a saline flow conductivity (SFC) of 5×10$^{-7}$ cm$^3$s/g.

The number of dust particles of example 4a before and after the pneumatic conveying is collated in table 1.

Example 4 b

The conveying output in the subsequent second conveying operation was 11.2 t/h of superabsorbent particles, the speed of the star feeder was 20 rpm, the conveying air rate was 660 m$^3$ (STP)/h, and the gas velocity was now 11.0 m/s at the start of the conveying conduit and 20.4 m/s at the end of the conveying conduit. The pressure in the conveying conduit was from 910 to 0 mbar, based on the ambient pressure. During the conveying, the pressure fluctuations were ±50 mbar. The conveying material load was 14.2 kg/kg, and the Froude number at the start of the conveying was 11. During the stable conveying, the pressure fluctuations were ±50 mbar and the average pressure in the conveying was 825 mbar.

After the conveying, the superabsorbent had a centrifuge retention capacity (CRC) of 38.6 g/g, an absorption under a pressure of 21.0 g/cm$^2$ (AUL) of 33.6 g/g, an absorption under a pressure of 49.2 g/cm$^2$ (AUHL) of 25.3 g/g, a saline flow conductivity (SFC) of 4×10$^{-7}$ cm$^3$s/g.

Example 4 c

The conveying output in the subsequent third conveying operation was 16.4 t/h of superabsorbent particles, the speed of the star feeder was 30 rpm, the conveying air rate was 560 m$^3$ (STP)/h, and the gas velocity was now 10.6 m/s at the start of the conveying conduit and 23.1 m/s at the end of the conveying conduit. The pressure in the conveying conduit was from 1230 to 0 mbar, based on the ambient pressure. During the conveying, the pressure fluctuations were ±50 mbar. The conveying material load was 18.3 kg/kg, and the Froude number at the start of the conveying was 10. During the stable conveying, the pressure fluctuations were ±50 mbar and the average pressure in the conveying was 1160 mbar.

After the conveying, the superabsorbent had a centrifuge retention capacity (CRC) of 38.6 g/g, an absorption under a pressure of 21.0 g/cm$^2$ (AUL) of 33.0 g/g, an absorption under a pressure of 49.2 g/cm$^2$ (AUHL) of 24.2 g/g, a saline flow conductivity (SFC) of 4×10$^{-7}$ cm$^3$s/g.

Example 4 d

The conveying output in the subsequent fourth conveying operation was 20.8 t/h of superabsorbent particles, the speed of the star feeder was 40 rpm, the conveying air rate was 770 m$^3$ (STP)/h, and the gas velocity was now 9.1 m/s at the start of the conveying conduit and 23.2 m/s at the end of the conveying conduit. The pressure in the conveying conduit was from 1800 to 0 mbar, based on the ambient pressure. During the conveying, the pressure fluctuations were ±50 mbar. The conveying material load was 23.1 kg/kg, and the Froude number at the start of the conveying was 9. During the stable conveying, the pressure fluctuations were ±200 mbar and the average pressure in the conveying was 1500 mbar.

After the conveying, the superabsorbent had a centrifuge retention capacity (CRC) of 38.6 g/g, an absorption under a pressure of 21.0 g/cm$^2$ (AUL) of 32.8 g/g, an absorption under a pressure of 49.2 g/cm$^2$ (AUHL) of 23.9 g/g, a saline flow conductivity (SFC) of 3×10$^{-7}$ cm$^3$s/g.

Figure 5:
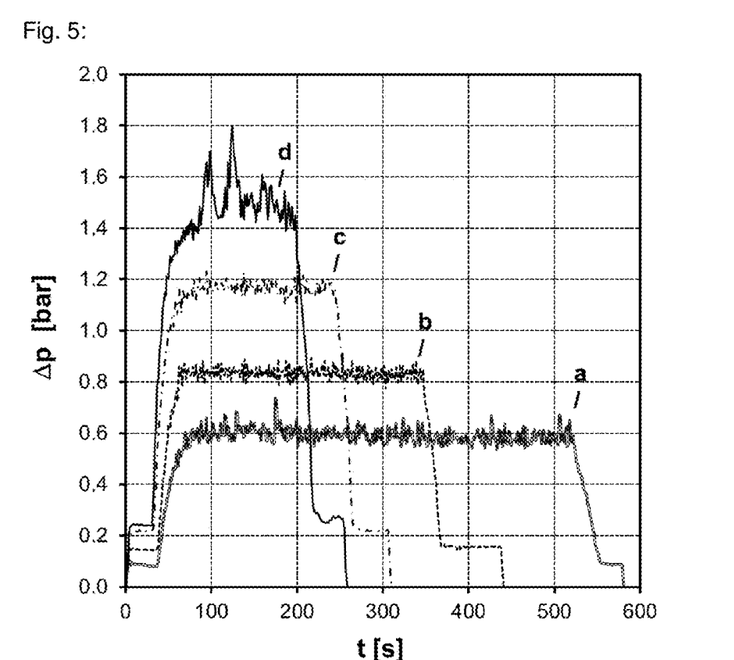

The starting pressure in the conveying conduit as a function of time in examples 4a to 4d is shown in FIG. 5.

TABLE 1

Normalized number of particles P discharged from the Heubach dustmeter in 5 l/min of dry air, normalized per min and per g of superabsorbent, classified and as sum total

| Example | Sample | Normalized particle number [P/min/g] | | | |
|---|---|---|---|---|---|
| | | <1 μm | 1 μm-10 μm | >10 μm | Sum total |
| 1 | before conveying | 60154 | 118915 | 3189 | 182258 |
| | after conveying | 81525 | 151647 | 4232 | 237404 |
| 2*) | before conveying | 126543 | 197421 | 3068 | 327032 |
| | after conveying | 266433 | 353877 | 6027 | 626337 |
| 3*) | before conveying | 419557 | 442039 | 3511 | 865107 |
| | after conveying | 682969 | 602259 | 4377 | 1289605 |
| 4a | before conveying | 27042 | 71293 | 2231 | 100566 |
| | after conveying | 52688 | 114416 | 5455 | 172559 |

*)comparative example

The invention claimed is:

1. A method of pneumatically conveying superabsorbent particles comprising admixing the superabsorbent particles with an aqueous wax dispersion prior to pneumatic conveying, wherein the wax has a glass transition temperature of at least 65° C. and, based on the untreated superabsorbent particles, from 0.020% to 0.20% by weight of wax is admixed.

2. The method according to claim 1, wherein the wax has a glass transition temperature of at least 80° C.

3. The method according to claim 1, wherein, based on the superabsorbent particles, from 0.035% to 0.08% by weight of wax is admixed.

4. The method according to claim 1, wherein the wax is a copolymer of 70 to 95 mol % of at least one ethylenically unsaturated hydrocarbon and 5 to 30 mol % of at least one ethylenically unsaturated carboxylic acid.

5. The method according to claim 1, wherein the superabsorbent particles have an average particle size of 250 to 500 μm.

6. The method according to claim 1, wherein the superabsorbent particles have an average sphericity (ASPHT) of greater than 0.72.

7. The method according to claim 1, wherein a temperature of the superabsorbent particles during the pneumatic conveying is at least 40° C., and at least 20° C. less than the glass transition temperature of the wax.

8. The method according to claim 1, wherein an initial gas velocity in the pneumatic conveying corresponds to a Froude number of 2 to 40.

9. The method according to claim 1, wherein a conveying material load in the pneumatic conveying is from 1 to 30 kg/kg and the conveying material load is the quotient of conveying material mass flow rate and gas mass flow rate.

10. A composition comprising superabsorbent particles and wax particles, wherein the wax particles are on the surface of the superabsorbent particles, the wax particles are dispersible in water and have a glass transition temperature of at least 65° C., a proportion of the wax particles based on the superabsorbent particles is from 0.02% to 0.2% by weight, and the composition has an absorption under a pressure of 4.83 kPa (AUL0.7 psi) of at least 10 g/g.

11. The composition according to claim 10, wherein the wax has a glass transition temperature of at least 80° C.

12. The composition according to claim 10, wherein, based on the superabsorbent particles, the proportion of wax particles is from 0.035% to 0.08% by weight of wax.

13. The composition according to claim 10, wherein the wax is a copolymer of 5 to 30 mol % of at least one ethylenically unsaturated carboxylic acid and 70 to 95 mol % of at least one ethylenically unsaturated hydrocarbon.

14. The composition according to claim 10, wherein the superabsorbent particles have an average particle size of 250 to 500 μm.

15. The composition according to claim 10, wherein the superabsorbent particles have an average sphericity (ASPHT) of greater than 0.72.

* * * * *